United States Patent
Choi et al.

(10) Patent No.: US 8,749,101 B2
(45) Date of Patent: Jun. 10, 2014

(54) CONTACT SH-GUIDED-WAVE MAGNETOSTRICTIVE TRANSDUCER

(75) Inventors: Myoung Seon Choi, Daegu (KR); Sung Joon Kim, Daegu (KR)

(73) Assignees: Industry-Academic Cooperation Foundation, Yeungnam University, Gyeongsan-si, Gyeongsanbuk-do (KR); Digital Ultrasonics Co. Ltd, Gyeongsan-si, Gyeongsanbuk-do (KR)

( * ) Notice: Subject to any disclaimer, the term of this patent is extended or adjusted under 35 U.S.C. 154(b) by 368 days.

(21) Appl. No.: 13/377,280

(22) PCT Filed: Jan. 15, 2010

(86) PCT No.: PCT/KR2010/000275
§ 371 (c)(1),
(2), (4) Date: Dec. 9, 2011

(87) PCT Pub. No.: WO2011/002139
PCT Pub. Date: Jan. 6, 2011

(65) Prior Publication Data
US 2012/0091829 A1    Apr. 19, 2012

(30) Foreign Application Priority Data
Jul. 3, 2009 (KR) .......................... 10-2009-0060758

(51) Int. Cl.
  *H01L 41/06* (2006.01)
  *H01L 41/12* (2006.01)
  *B06B 1/08* (2006.01)
  *G01N 29/46* (2006.01)
  *G01N 29/24* (2006.01)

(52) U.S. Cl.
  CPC ................ *H01L 41/06* (2013.01); *H01L 41/12* (2013.01); *B06B 1/08* (2013.01); *G01N 29/46* (2013.01); *G01N 29/2418* (2013.01); *G01N 2291/0422* (2013.01)
  USPC ................ 310/26; 310/23; 310/208; 324/209

(58) Field of Classification Search
  CPC ........... H01L 41/06; H01L 41/12; B06B 1/08; G01N 29/46; G01N 29/2418; G01N 2291/0422
  USPC ............................... 310/23, 26, 208; 324/209
  IPC .......................... H01L 41/06, 41/12; B06B 1/08
  See application file for complete search history.

(56) References Cited

U.S. PATENT DOCUMENTS 2,728,063 A * 12/1955 Renner ........................ 367/168
3,174,130 A *  3/1965 Woollett ..................... 367/168

(Continued)

FOREIGN PATENT DOCUMENTS

JP    56-004914    1/1981
JP    56-040742    4/1981

(Continued)

*Primary Examiner* — John K Kim
(74) *Attorney, Agent, or Firm* — Sherr & Jiang, PLLC

(57) ABSTRACT

A contact shear horizontal (SH) mode guided-wave magnetostrictive transducer including: a transduction band which is disposed on a surface of an object to be tested and in which electromagnetic acoustic transduction occurs; and radio frequency (RF) coils disposed on the transduction band, wherein the transduction band includes a plate-shaped solenoid including a magnetostrictive strip in which the electromagnetic acoustic transduction for transmitting or receiving SH mode guided waves occurs, and solenoid coil wound in a spiral form along a circumference of the magnetostrictive strip so as to form a bias magnetic field in a lengthwise direction of the magnetostrictive strip, and the RF coils are used to form a dynamic magnetic field in a widthwise direction of the magnetostrictive strip or to detect a change of magnetic flux in the magnetostrictive strip.

11 Claims, 4 Drawing Sheets

(56) References Cited

U.S. PATENT DOCUMENTS

| | | | |
|---|---|---|---|
| 3,470,402 A * | 9/1969 | Abbott | 310/26 |
| 4,720,676 A * | 1/1988 | Anderson et al. | 324/207.17 |
| 4,920,806 A | 5/1990 | Obama et al. | |
| 5,305,075 A * | 4/1994 | Bucholtz et al. | 356/477 |
| 5,581,037 A * | 12/1996 | Kwun et al. | 73/623 |
| 6,000,288 A * | 12/1999 | Kwun et al. | 73/597 |
| 6,344,743 B1 * | 2/2002 | Holmes et al. | 324/250 |
| 6,396,262 B2 * | 5/2002 | Light et al. | 324/240 |
| 6,429,650 B1 * | 8/2002 | Kwun et al. | 324/240 |
| 6,624,628 B1 * | 9/2003 | Kwun et al. | 324/240 |
| 6,917,196 B2 * | 7/2005 | Kwun et al. | 324/240 |
| 6,924,642 B1 | 8/2005 | Cho et al. | |
| 7,295,001 B2 * | 11/2007 | Kim et al. | 324/209 |
| 2004/0095137 A1 * | 5/2004 | Kwun et al. | 324/240 |
| 2005/0179430 A1 * | 8/2005 | Park et al. | 324/240 |
| 2007/0179430 A1 * | 8/2007 | Smith et al. | 604/20 |
| 2012/0091829 A1 * | 4/2012 | Choi et al. | 310/26 |

FOREIGN PATENT DOCUMENTS

| | | |
|---|---|---|
| JP | 01-212301 | 8/1989 |
| KR | 10-0561215 | 3/2006 |
| KR | 10-0683927 | 2/2007 |

* cited by examiner (a)

(b)

US 8,749,101 B2

CONTACT SH-GUIDED-WAVE MAGNETOSTRICTIVE TRANSDUCER

CROSS REFERENCE TO PRIOR APPLICATIONS

This application is a National Stage Patent Application of PCT International Patent Application No. PCT/KR2010/000275 (filed on Jan. 15, 2010) under 35 U.S.C. §371, which claims priority to Korean Patent Application No. 10-2009-0060758 (filed on Jul. 3, 2009), which are all hereby incorporated by reference in their entirety.

TECHNICAL FIELD

The present invention relates to a contact shear horizontal (SH) mode guided-wave magnetostrictive transducer, and more particularly, to a magnetostrictive guided-wave transducer that is used for long-range ultrasonic nondestructive inspection of an industrial structure.

BACKGROUND ART

SH mode guided waves are elastic waves that have displacement of particles that is parallel to the surface of a structure, are guided by the structural boundary, and are propagated at a large distance. The SH mode guided waves have advantages in that they are insensitive to a fluid that may exist on an inside or outside surface of the structure and a possibility of mode conversion is low when interacting with discontinuities and thus they allow a simple echo structure that can be easily interpreted during long-range ultrasonic inspection. SH0 mode and T(0,1) mode guided waves are particularly useful in a flat plate or a plate-shaped structure having curvature and a cylindrical structure, respectively, since they have non-dispersive characteristics that their speeds of propagation are not varied according to wave frequencies. In related arts, these waves are generated or detected using a piezoelectric array transducer and two kinds of electromagnetic acoustic transducers (EMATs), i.e., a periodically polarized magnet (PPM) EMAT and a magnetostrictive transducer. The magnetostrictive transducer has a simpler structure than the piezoelectric array transducer and the PPM EMAT.

For transmission of the SH mode guided waves, the magnetostrictive transducer relies on deformation of ferromagnetic material due to overlapping of a bias static magnetic field and a dynamic magnetic field that are perpendicular to each other in a portion that is near a lower portion of the surface of the ferromagnetic material. The bias field is provided by a permanent magnet or an electromagnet to the ferromagnetic material, and the dynamic field is provided by coils through which an alternating current (AC) pulse in an RF band flows, so-called radio frequency (RF) coils to the ferromagnetic material. Due to skin effect of the dynamic magnetic field, a wave source is limited to the vicinity of the surface of the ferromagnetic material. A guided wave mode propagating along the structure mainly depends on the characteristic of the wave source and the thickness of the structure. During reception of the SH mode guided waves, the RF coils are used to detect a change of magnetic flux that is generated in the material due to the waves. When an object to be tested is formed of a ferromagnetic material, the object itself can be used as an element of a transducer so that the SH mode guided waves can be generated in the ferromagnetic material and detected without direct contact between other two elements (coils and magnet) and the object. Such non-contact magnetostrictive transducers allow high-temperature inspection. Low frequency SH-guided-waves have been transmitted and received by an elongated-spiral coil transducer, while high frequency SH-guided-waves have been transmitted and received by a meanderline coil transducer or a multi-spiral coil transducer. These magnetostrictive transducers include permanent magnets or electromagnets that generate a static magnetic field that is parallel to a direction of a leg portion of each RF coil and thus is perpendicular to a dynamic magnetic field.

In a non-ferromagnetic object, the SH mode guided waves may be transmitted and received by using contact magnetostrictive transducers each including a magnetostrictive strip (or magnetostrictive patch) that is temporarily or permanently adhered to the surface of the non-ferromagnetic object. These contact magnetostrictive transducers have also been applied to the ferromagnetic material for more efficient transmission and reception of the SH mode guided waves. In related arts, residual magnetization in the lengthwise direction of the magnetostrictive strip that is obtained by moving a U-shaped permanent magnet along the magnetostrictive strip that is adhered to a structure using a sticky material such as epoxy, has been used as a bias static magnetic field. In the contact magnetostrictive transducers, low frequency (generally less 200 kHz) SH mode guided waves propagating in the widthwise direction of the magnetostrictive strip can be efficiently transmitted or received. Thus, the contact magnetostrictive transducers have been widely used in long-range ultrasonic inspection of a large-sized structure. However, these conventional magnetostrictive strip guided-wave transducers have the following drawbacks. First, when the magnetostrictive strip is detached from the object to be tested or when epoxy firmly adhered to the detached strip is removed, the magnetostrictive strip may be easily damaged and thus, it is difficult to reuse the magnetostrictive strip repeatedly. Second, in case of a strip adhered to an object having large curvature such as a pipe having a small diameter or a non-ferromagnetic pipe such as an aluminum pipe, it is difficult to obtain uniform residual magnetization. Third, a strong dynamic magnetic field may cause a irreversible change of residual magnetization and thus, currents that flow through the RF coils during transmission of the SH-guided waves need to be limited to a certain range. Since the impedance of the RF coils is proportional to frequency, limitation of currents that flow through coils driven at relatively lower frequency becomes severe. Furthermore, the limitation is not easily quantified. This means that considerable cautions are needed for correct use of the magnetostrictive strip guided-wave transducers. Fourth, it is difficult to control intensity of residual magnetization. This implies that for construction of a transducer presenting a linear response with respect to a change of the dynamic magnetic field, the use of an optimized bias magnetic field is rarely possible.

DISCLOSURE OF INVENTION

Technical Problem

The present invention provides a contact SH mode guided-wave magnetostrictive transducer that includes a unit for forming a bias magnetic field itself and for forming a uniform and controllable bias magnetic field in a magnetostrictive strip so that the contact SH-guided-wave transducer can reversibly react with a change of a dynamic magnetic field.

Technical Solution

According to an aspect of the present invention, there is provided a contact SH mode guided-wave magnetostrictive transducer including: a transduction band which is disposed on a surface of an object to be tested and in which electromagnetic acoustic transduction occurs; and radio frequency (RF) coils disposed on the transduction band, wherein the transduction band includes a plate-shaped solenoid including a magnetostrictive strip in which the electromagnetic acoustic transduction for transmitting or receiving SH mode guided waves occurs, and a solenoid coil wound in a spiral form along a circumference of the magnetostrictive strip so as to form a bias magnetic field in a lengthwise direction of the magnetostrictive strip, and the RF coils are used to form a dynamic magnetic field in a widthwise direction of the magnetostrictive strip or to detect a change of magnetic flux in the magnetostrictive strip.

The transduction band may be disposed to surround the object to be tested while being closely adhered to the surface of the object to be tested. The solenoid coil may surround the circumference of the magnetostrictive strip uniformly and may form a uniform and controllable bias magnetic field with respect to the lengthwise direction of the magnetostrictive strip.

The transduction band may further include a non-ferromagnetic metal strip disposed to be acoustically coupled to a lower surface of the plate-shaped solenoid so that a shape of the transduction band is maintained and the magnetostrictive strip and the solenoids are prevented from being damaged. The transduction band may further include a contact layer coated on a lower surface of the plate-shaped solenoid and including a non-stickiness material that allows the transduction band to be repeatedly attached and detached to and from the surface of the object to be tested and the transduction band to be reused. Also, the transduction band may further include a contact layer coated on a lower surface of the non-ferromagnetic metal strip and including a non-stickiness material that allows the transduction band to be repeatedly attached and detached to and from the surface of the object to be tested and the transduction band to be reused. The contact layer may include material having an excellent transverse wave propagation characteristic and an electrical insulation property.

The object to be tested may include a cylindrical structure having a circular cross-section, and the transduction band may contact the surface of the object to be tested and may have a ring-shaped cross-section in which both ends of the transduction band face each other, and as the non-ferromagnetic metal strip has a larger length than that of the magnetostrictive strip, when the non-ferromagnetic metal strip is adhered to the lower surface of the plate-shaped solenoid and is coupled to the lower surface of the plate-shaped solenoid, both ends of the non-ferromagnetic metal strip may be exposed to the outside. In this case, the transduction band may include: a contact layer disposed between the surface of the object to be tested and the lower surface of the non-ferromagnetic metal strip; and a clamping unit for coupling the both ends of the non-ferromagnetic metal strip. The both ends of the non-ferromagnetic metal strip may be respectively bent and may form a pair of ring portions for facing each other, and the clamping unit may include: a pair of cylinders in which through holes through which bolts are tightened are formed and which are inserted in the pair of ring portions; and a bolting unit for tightly coupling the pair of metal cylinders through the through holes. The contact layer may include metal or plastic that is easily deformable and flexible so that acoustic coupling between the object to be tested and the non-ferromagnetic metal strip is easily performed.

Advantageous Effects

The transduction band including a plate-shaped solenoid is used so that a uniform, robust and controllable bias magnetic field can be formed in a magnetostrictive strip without an additional unit and the contact SH-guided-wave magnetostrictive transducer having a reversible response to a change of a dynamic magnetic field can be constituted. An optimized contact SH-guided-wave magnetostrictive transducer that has a high reliability and gives a linear response to the change of the dynamic magnetic field can be used.

BRIEF DESCRIPTION OF DRAWINGS

The above and other aspects of the present invention will become more apparent by describing in detail exemplary embodiments thereof with reference to the attached drawings in which.

BEST MODE FOR CARRYING OUT THE INVENTION

The present invention will now be described more fully with reference to the accompanying drawings, in which exemplary embodiments of the invention are shown.

Figure 1:
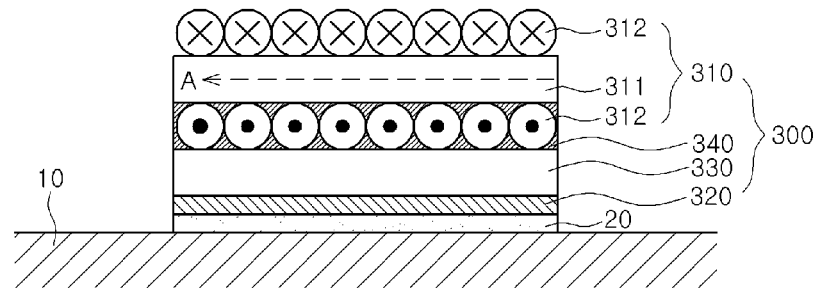
FIG. 1 is a cross-sectional view of a transduction band of a contact shear horizontal (SH) mode guided-wave magnetostrictive transducer according to an embodiment of the present invention.
Figure 2:
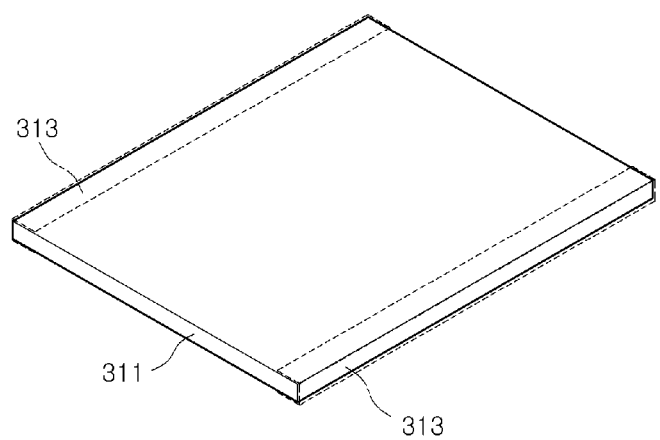
FIG. 2 is a perspective view of a plate-shaped solenoid of the contact SH-guided-wave magnetostrictive transducer of FIG. 1.
Figure 2:
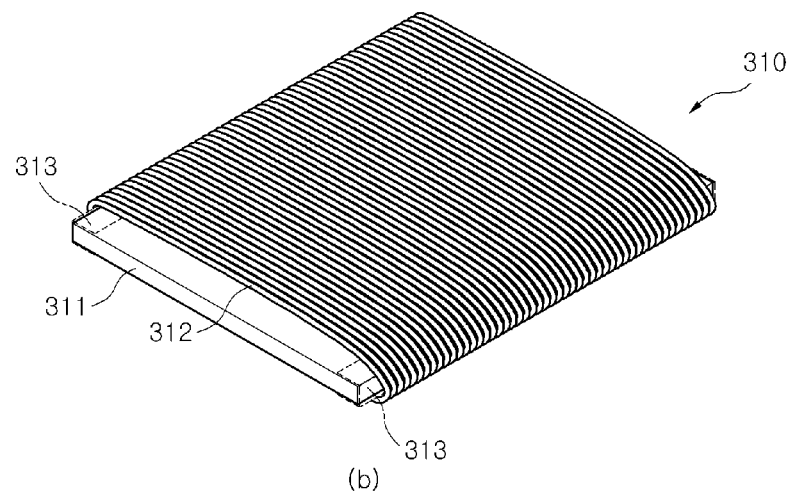
Figure 3:
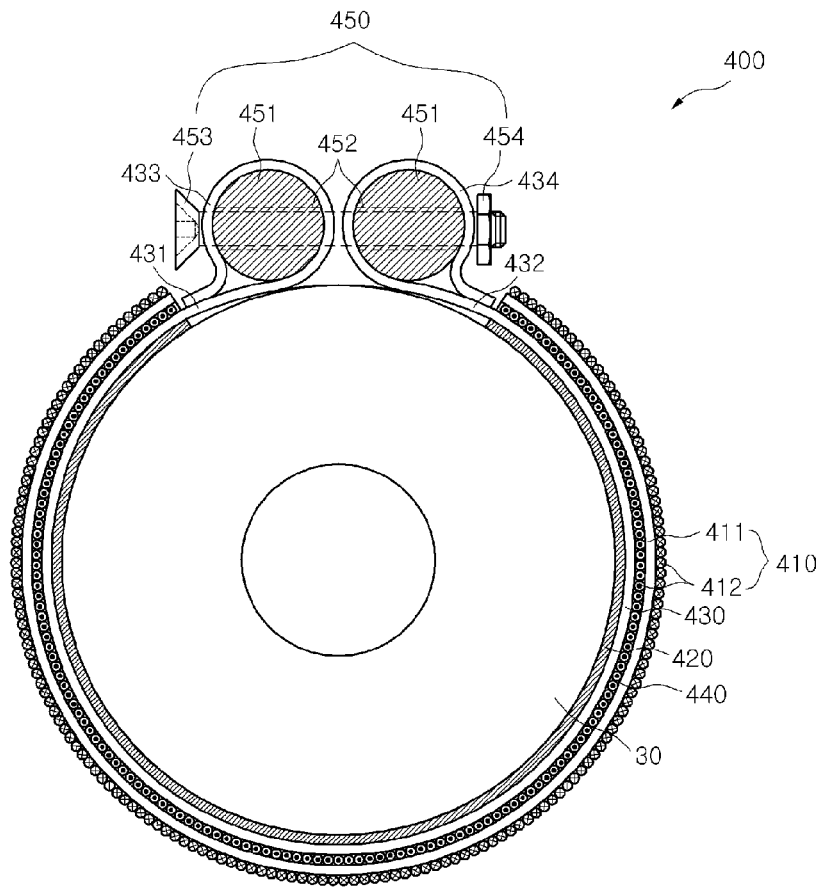
FIG. 3 is a cross-sectional view illustrating installation of a ring-shaped transduction band of a contact SH-guided-wave magnetostrictive transducer according to another embodiment of the present invention.

FIG. 1 is a cross-sectional view of a transduction band 300 of a contact shear horizontal (SH) mode guided-wave magnetostrictive transducer according to an embodiment of the present invention, and FIG. 2 is a perspective view of a plate-shaped solenoid 310 of the contact SH-guided-wave magnetostrictive transducer of FIG. 1, and FIG. 3 is a cross-sectional view illustrating installation of a ring-shaped transduction band 400 of a contact SH-guided-wave magnetostrictive transducer according to another embodiment of the present invention.

Referring to FIGS. 1 through 3, the contact SH-guided-wave magnetostrictive transducer includes two parts, i.e., two transduction bands 300 and 400 and RF coils (not shown). The transduction bands 300 and 400 that are one part of the contact SH-guided-wave magnetostrictive transducer are disposed on surfaces of two objects to be tested 10 and 30, are acoustically coupled to the surfaces of the objects to be tested 10 and 30, and electromagnetic acoustic transduction occurs in the transduction bands 300 and 400. The transduction bands 300 and 400 may be acoustically coupled to the surfaces of the objects to be tested 10 and 30 by using a sticky material such as epoxy or the like. Liquids having an excellent transverse wave propagation characteristic such as grain syrup or honey may be used as an alternative of epoxy, even though they are relatively less sticky and provides coupling intensity that depends on time or temperature. The RF coils (not shown) that are the other part of the contact SH-guided-wave magnetostrictive transducer are disposed on the transduction bands 300 and 400 and detect a change of magnetic flux generated in magnetostrictive strips 311 and 411 due to SH mode guided waves.

FIG. 1 illustrates a lengthwise cross-section of the transduction band 300 adhered to the flat object to be tested 10. The transduction band 300 is not limitatively used in the flat object to be tested 10. When an object to be tested forms a curved surface such as a pipe-shaped object, the transduction band 300 may be disposed to surround the object to be tested while being closely adhered to the surface of the object to be tested. In order to acoustically couple the transduction band 300 and the object to be tested 10 to each other, a coupling material 20 having an excellent transverse wave propagation characteristic is used.

The transduction band 300 includes the plate-shaped solenoid 310 including the magnetostrictive strip 311 and a solenoid coil 312, a non-ferromagnetic metal strip 330, and a contact layer 320. The transduction band 300 may also include the magnetostrictive strip 311, the plate-shaped solenoid 310, and the contact layer 320 without inclusion of the non-ferromagnetic metal strip 330.

The transduction band 300 includes a structure of the plate-shaped solenoid 310 that is a unit for forming a bias magnetic field in the magnetostrictive strip 311. In detail, the plate-shaped solenoid 310 includes the magnetostrictive strip 311 and the solenoid coil 312 and thus forms the uniform, robust and controllable bias magnetic field in the lengthwise direction (direction A of FIG. 1) of the magnetostrictive strip 311 without using an additional unit.

The structure of the plate-shaped solenoid 310 will now be described with reference to FIG. 2 in more detail. Electromagnetic acoustic transduction for transmission and reception of the SH mode guided waves occurs in the magnetostrictive strip 311. In this case, the RF coils (not shown) are used to form a dynamic magnetic field in a widthwise direction of the magnetostrictive strip 311 (in a direction perpendicular to the direction A on a plane of the magnetostrictive strip 311 of FIG. 1, i.e., in a forward or backward direction that is a direction in which the RF coils are vertically inserted or removed in or from the cross-section of the magnetostrictive strip 311) or to detect a change of magnetic flux in the magnetostrictive strip 311.

In addition, the solenoid coil 312 is constituted by tightly winding an insulating electric wire such as an enamel copper wire in a spiral form along the circumference of the magnetostrictive strip 311 so that the bias magnetic field may be formed in the lengthwise direction (direction A of FIG. 1) of the magnetostrictive strip 311. The solenoid coil 312 uniformly surrounds the circumference of the magnetostrictive strip 311 and thus, the uniform and controllable bias magnetic field is formed in the lengthwise direction of the magnetostrictive strip 311 so that a magnetostrictive transducer for providing a reversible response to the change of the dynamic magnetic field may be realized. The reversible response of the magnetostrictive transducer using the transduction band 300 will be introduced later by representing experimental data. As described above, a direct current (DC) is flown through the solenoid coil 312 so that the uniform, robust and controllable bias magnetic field may be formed in the lengthwise direction of the magnetostrictive strip 311.

When the solenoid coil 312 is wound, electrical short between the electric wire portion of the solenoid coil 312 and the magnetostrictive strip 311 may occur at both sharp edges of the magnetostrictive strip 311 due to damage of an insulation film. In order to prevent this electrical short, a thin both-sided tape 313 having very excellent electrical insulation property and heat-resistant property such as a polyimide tape may be attached to the both edges of the magnetostrictive strip 311. The both-sided tape 313 is conducive to uniform winding of the electric wire portion of the solenoid coil 312 on the magnetostrictive strip 311 due to its stickiness while the solenoid coil 312 surrounds the circumference of the magnetostrictive strip 311. In order to manufacture the more elaborate and thinner plate-shaped solenoid 310, printing circuit technology or the like may be used.

The transduction band 300 includes the non-ferromagnetic metal strip 330 and the contact layer 320, which are formed below the plate-shaped solenoid 310. The non-ferromagnetic metal strip 330 of the transduction band 300 has a slightly larger surface than a surface of the magnetostrictive strip 311. The non-ferromagnetic metal strip 330 is adhered to the plate-shaped solenoid 310 by using an adhesive layer 340 such as an epoxy layer so that the non-ferromagnetic metal strip 330 may be acoustically coupled to a lower surface of the plate-shaped solenoid 310. Thus, the shape of the transduction band 300 is maintained, and the magnetostrictive strip 311 and the solenoid coil 312 are prevented from being damaged. Thus, the transduction band 300 may be deformed within an elasticity limitation with geometry that is adapted to the surface of the object to be tested 10. The elasticity limitation depends on materials and thicknesses of the non-ferromagnetic metal strip 330 and the adhesive layer 340.

The contact layer 320 is coated on a lower surface of the non-ferromagnetic metal strip 330 and is formed of a non-stickiness material that allows the transduction band 300 to be repeatedly attached and detached to and from the surface of the object to be tested 10 and the transduction band 300 to be reused. For example, for case that an adhesive material such as epoxy is used as the coupling material 20, the contact layer 320 may be formed by firmly coating material having excellent non-stickiness, a good transverse wave propagation characteristic and an electrical insulation property such as Teflon to a thickness of several tens of micrometers. Thus, although acoustic coupling between the transduction band 300 and the object to be tested 10 is performed by using epoxy, due to the non-stickiness of the contact layer 320, the transduction band 300 may be easily detached from the surface of the object to be tested 10 without any damage and the transduction band 300 may be repeatedly reused. Also, the electrical insulation property of the contact layer 320 prevents occurrence of a non-uniform eddy current that is generated by electrical coupling between the non-ferromagnetic metal strip 330 and the object to be tested 10.

In order to prevent the occurrence of the eddy current in the magnetostrictive strip 311, the magnetostrictive strip 311 having a smaller thickness than a depth of penetration of the dynamic magnetic field formed by the RF coils disposed on the transduction band 300 may be used. In order to minimize deformation of the SH mode guided waves in the transduction band 300, the thickness of the transduction band 300 needs to be much smaller than a wavelength of the guided waves. Thus, as frequency of the guided waves increases, the use of a thinner transduction band is needed. In most metal structures, the propagation speeds of fundamental mode guided waves are about 3000 m/s. In the frequency range (20 to 200 kHz) that is mainly used in the field of long-range ultrasonic inspection, therefore, the wavelength of the guided waves is about 15 to 150 mm. This implies that the transduction band 300 may be easily manufactured.

In a cylindrical structure having a circular cross-section such as a pipe, a transduction band for a contact SH-guided-wave transducer for transmitting and receiving a torsional mode (T-mode) guided waves that proceed in an axial direction of the cylindrical structure may be ring-shaped. FIG. 3 represents an example of the transduction band 400 according to another embodiment of the present invention in which the structure of the transduction band 300 is applied to the object to be tested 30 having a circular shape. In detail, the object to be tested 30 is a cylindrical structure having a circular cross-section. In addition, the transduction band 400 is acoustically coupled to the surface of the object to be tested 30 by using a clamping unit 450, contacts the surface of the object to be tested 30 and thus has a ring-shaped cross-section in which both ends of the transduction band 400 face each other.

FIG. 3 illustrates a shape in which the lengthwise portion of the transduction band 400 is wound in a circumferential direction of the object to be tested 30. In this case, the lengthwise portion of the magnetostrictive strip 411 is also wound in the circumferential direction of the object to be tested 30. Thus, a bias magnetic field formed in the lengthwise direction of the magnetostrictive strip 411 is formed in a direction that corresponds to the circumferential direction of the object to be tested 30 in the magnetostrictive strip 411. Also, a dynamic magnetic field formed in the widthwise direction of the magnetostrictive strip 411 is formed in a direction that corresponds to the axial direction of the object to be tested 30 in the magnetostrictive strip 411.

The transduction band 400 includes a plate-shaped solenoid 410 including the magentostrictive strip 411 and a solenoid coil 412, a non-ferromagnetic metal strip 430, an adhesive layer 440 such as an epoxy layer between the non-ferromagnetic metal strip 430 and the plate-shaped solenoid 410, and a contact layer 420 that directly contacts the surface of the object to be tested 30. The contact layer 420 is disposed between the surface of the object to be tested 30 and a lower surface of the non-ferromagnetic metal strip 430 and may be formed of metal or plastic that is easily deformable and flexible so that acoustic coupling between the object to be tested 30 and the non-ferromagnetic metal strip 430 may be easily performed. For example, the contact layer 420 may be formed using a shim formed of metal such as aluminum (Al) or brass so that acoustic coupling between the object to be tested 30 and the non-ferromagnetic metal strip 430 may be easily achieved.

As the non-ferromagnetic metal strip 430 has a larger length than that of the magnetostrictive strip 411, when the non-ferromagnetic metal strip 430 is adhered to the lower surface of the plate-shaped solenoid 410 and is coupled thereto, both ends 431 and 432 of the non-ferromagnetic metal strip 430 are exposed to the outside. The non-ferromagnetic metal strip 430 is formed of material having larger mechanical strength than the plate-shaped solenoid 410, and a clamping unit 450 is installed on the both ends 431 and 432 of the non-ferromagnetic metal strip 430. The clamping unit 450 allows dry coupling between the transduction band 400 and the object to be tested 30 as the exposed both ends 431 and 432 of the non-ferromagnetic metal strip 430 are coupled to each other. More specifically, for the above-described dry coupling, the exposed both ends 431 and 432 of the non-ferromagnetic metal strip 430 are respectively bent, thereby forming a pair of ring portions 433 and 434 that face each other. In this case, the clamping unit 450 includes a pair of metal cylinders 451 and a bolting unit 453. Through holes 452 through which bolts are tightened, are formed in the pair of metal cylinders 451, and the metal cylinders 451 are respectively inserted in the pair of ring portions 433 and 434, and the bolting unit 453 tightly couples the metal cylinders 451 through the through holes 452, and a nut 454 is additionally used thereto. In detail, tightening of the bolting unit 453 and the nut 454 through the through holes 452 formed in the middle of the two metal cylinders 451 induces efficient and easy dry coupling between the transduction band 400 and the pipe-shaped object to be tested 30. The ring portions 433 and 434 that are both ends of the non-ferromagnetic metal strip 430 are connected to each other to surround the metal cylinders 451, and as stronger tightening of the ring portions 433 and 434 is performed, surfaces formed directly on the both ends 431 and 432 of the non-ferromagnetic metal strip 430 that face each other are welded each other.

Figure 4:
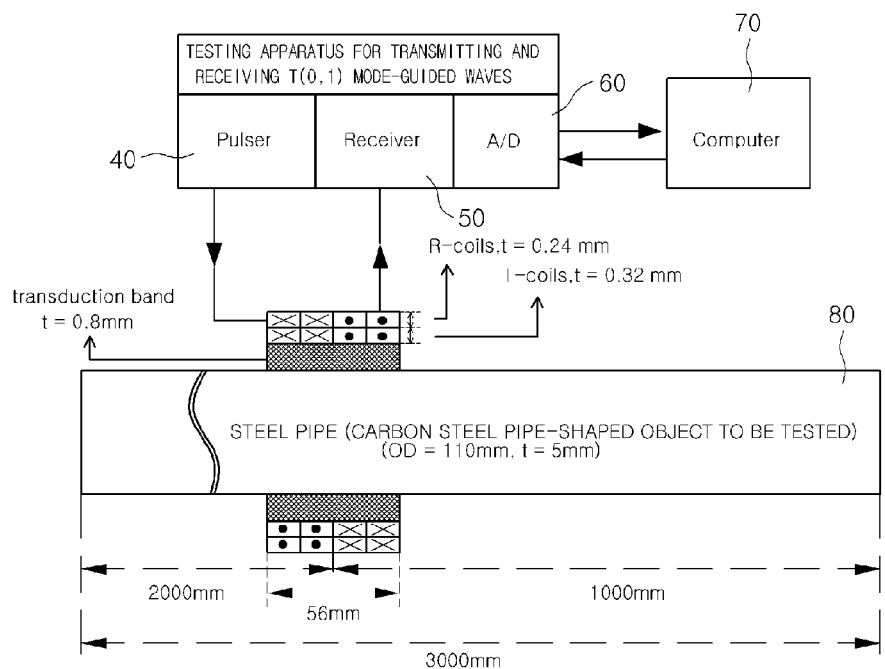
FIG. 4 is a schematic diagram of a testing apparatus for transmitting and receiving T(0,1) mode guided waves in a pipe-shaped object to be tested.
Figure 5:
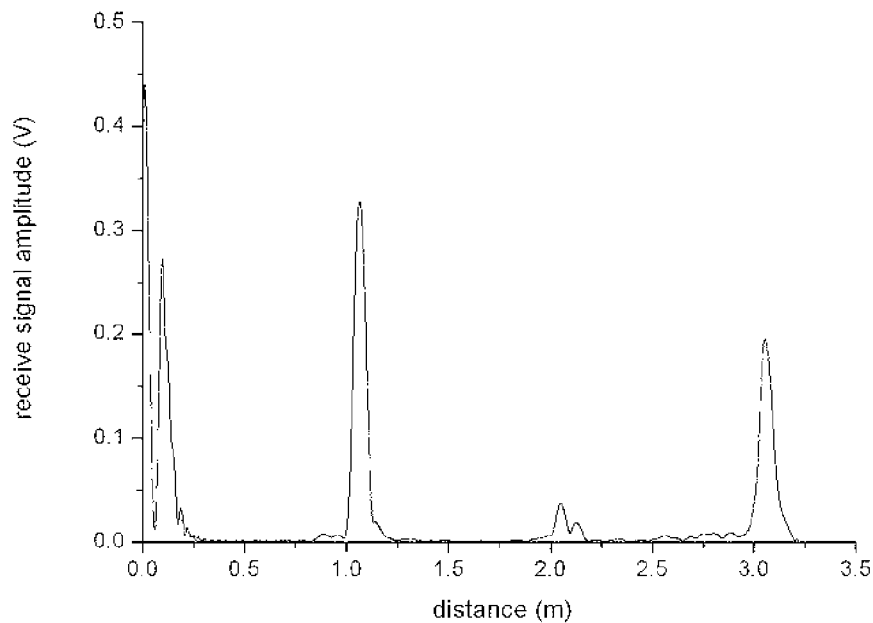
FIG. 5 is a graph showing signal data that is obtained through experiments of FIG. 4.
Figure 6:
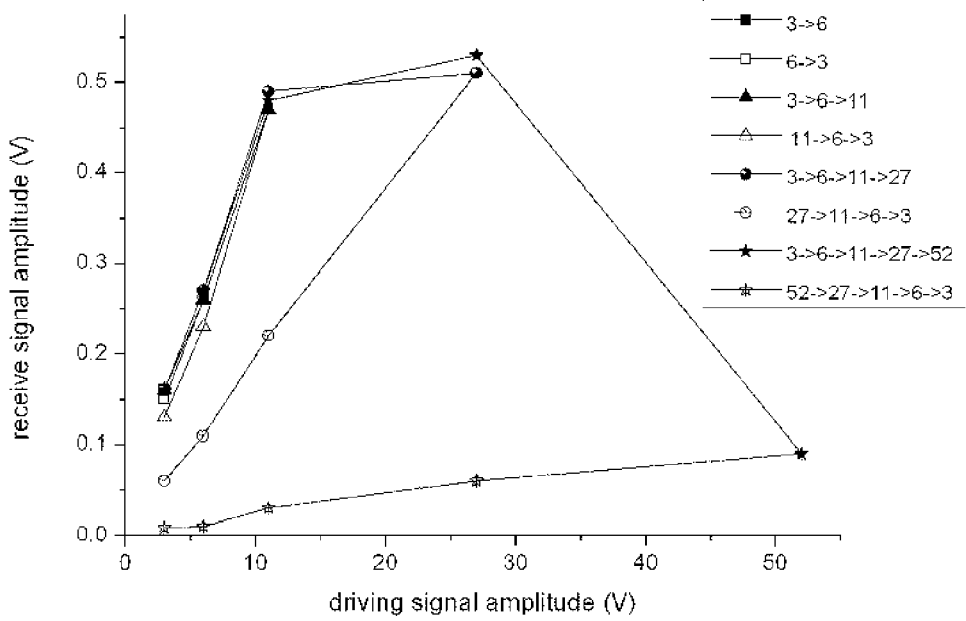
FIG. 6 is a graph showing a response to a transmission coil driving signal of a conventional contact SH-guided-wave magnetostrictive transducer.
Figure 7:
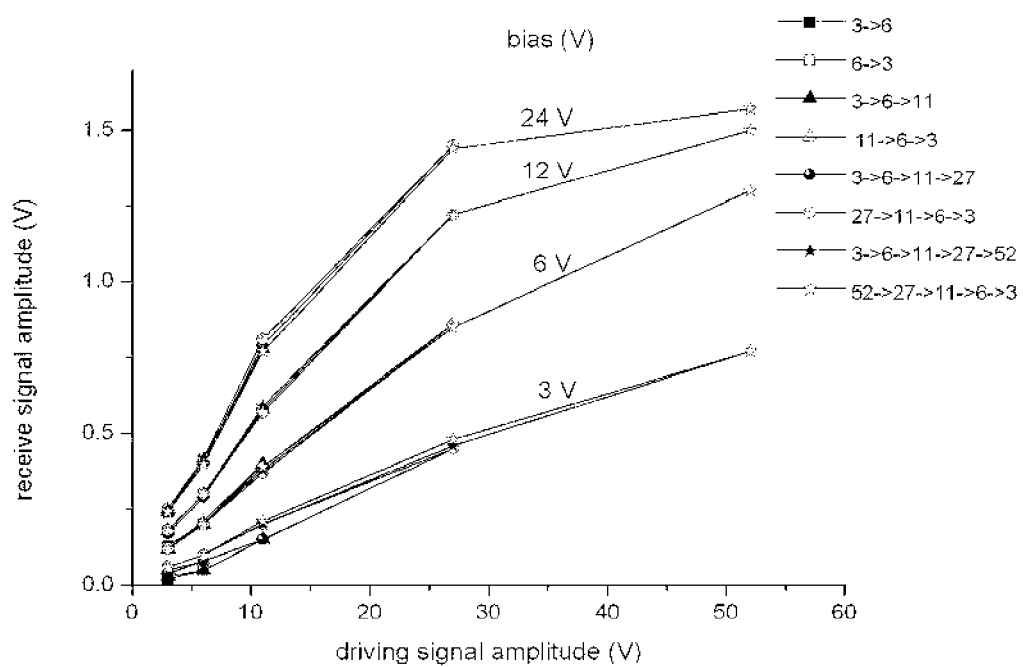
FIG. 7 is a graph showing a response to a transmission coil driving signal and a bias voltage of the contact SH-guided-wave magnetostrictive transducer including the transduction band of FIG. 1.

Hereinafter, experimental data for verifying effectiveness of the present invention will be introduced with reference to FIGS. 4 through 7. FIG. 4 is a schematic diagram of a testing apparatus for transmitting and receiving T(0,1) mode guided waves in a pipe-shaped object to be tested 80. In this case, the transduction band 300 of FIG. 1 is used as an object to be experimented. FIG. 5 is a typical graph showing signal data that is obtained through experiments of FIG. 4. FIG. 6 is a graph showing a response to a transmission coil driving signal of a conventional contact SH-guided-wave magnetostrictive transducer, and FIG. 7 is a graph showing a response to a transmission coil driving signal and a bias voltage of the contact SH-guided-wave magnetostrictive transducer including the transduction band 300 of FIG. 1.

In order to verify the above-described effectiveness, carbon steel pipe having an outer diameter of 110 mm, a thickness of 5 mm and a length of 3 m was used as the object to be tested 80, and two kinds of magnetostrictive transducers that transmit and receive T(0,1) mode guided waves in the object to be tested 80 were manufactured. FIG. 4 illustrates the testing apparatus for evaluating transduction efficiency of the two kinds of magnetostrictive transducers. Each of the two magnetostrictive transducers included a transduction band (indicated by a hatching portion) that was adhered to the surface of pipe 80 along a circumferential direction of pipe 80 in a position that corresponds to a one third portion of the length of pipe 80, a transmission RF coil array (T-coils) and a received RF coil array (R-coils), which were overlapped with each other and disposed on the transduction band. The manufactured magnetostrictive transducers were classified according to types of transduction bands used therein. Also, one transmission coil array (T-coils) and one received coil array (R-coils) were commonly used for all of the magnetostrictive transducers.

One of two kinds of transduction bands was a magnetostrictive strip itself. A magnetostrictive transducer including a transduction band (not shown) that is the magnetostrictive strip itself represents the conventional transducers in related arts. The other one of the transduction bands was the transduction band 300 of FIG. 1. The magnetostrictive strip that was used in the magnetostrictive transducer including a conventional transduction band (not shown) that was the magnetostrictive strip itself was an iron-cobalt alloy Hyperco50HS strip (width of 56 mm×length of 310 mm×thickness of 0.1 mm) that was supplied by Carpenter Technology Corporation, located in U.S.A. The magnetostrictive strip has been known to have large residual magnetization of 14 kG and a coercive force of 25 Oe that may be used to generate a bias magnetic field. The magnetostrictive strip 311 included in the transduction band 300 of FIG. 1 was an iron-cobalt alloy Vacoflux50 strip (width of 56 mm×length of 310 mm×thickness of 0.1 mm) that was supplied by Vacuumschmeltz GmbH, located in Germany. The strip had very low residual magnetization of 2.1 kG and a coercive force of 3 Oe. Thus, it was difficult that residual magnetization was used to generate the bias magnetic field. The contact layer 320 of the transduction band 300 was formed of Teflon, and its thickness was about 20 micrometers. The non-ferromagnetic metal strip 330 of the transduction band 300 was an aluminum (Al) strip (width of 60 mm×length of 316 mm×thickness of 0.2 mm). Also, the solenoid coil 312 of the transduction band 300 was formed of an enameled copper wire having a diameter of 0.15 mm, and a DC resistance of the solenoid coil 312 was 93Ω.

Each of the transmission coil array (T-coils) and the received coil array (R-coils) included two identical elongated-spiral coils that were arranged so that one leg portion of one coil might be disposed in the middle of two leg portions of the other coil. The transmission coils were formed of a rectangular enameled copper wire (width of 1.3 mm×thickness of 0.20 mm), and the number of winding was 10. The received coils were formed of an enameled copper wire having a diameter of 0.12 mm, and the number of winding was 110. The width and length of a leg portion of all of the spiral coils and a distance between two leg portions thereof were 14 mm, 500 mm, and 28 mm, respectively. The width and the distance were selected in consideration of a propagation speed of 2880 m/s of the T(0,1) mode so that the width and the distance might be almost the same as ¼ wavelength and ½ wavelength of the guided waves at a frequency of 50 kHz in the magnetostrictive strip. Thus, the entire width of each coil array and the width of the magnetostrictive strip were 56 mm that was the same as one wavelength of the guided waves.

The testing apparatus for transmitting and receiving T(0,1) mode guided waves in a pipe 80, illustrated in FIG. 4, was a GWR320 system supplied by a Digital Ultrasonics Co., Ltd. The GWR320 system allows two transmission coils and two received coils to be disposed according to a phased array theory and thus may adjust the proceeding direction of transmission guided waves and the detection direction of received guided waves. In the present experiments, a pulser 40 was adjusted so that two driving voltage signals having the same output waveform (50 kHz, a rectangular pulse of two cycles) and completely different (i.e., opposite) phases were supplied to two terminals of each transmission coils, and an RF signal induced to both ends of received coils was converted into a video signal via a band width pass filter of a receiver 50 and an analog to digital (A/D) converter 60 and was stored in a computer 70.

Experimental procedures of the magnetostrictive transducer including the conventional transduction band (not shown) that includes only the magnetostrictive strip were as below. 1) A transduction band was adhered to the sample pipe 80 by using five-minute epoxy. 2) Residual magnetization was induced into the magnetostrictive strip by using a permanent magnet. 3) A transmission coil array (T-coils) and a received coil array (R-coils) were disposed on the transduction band and then were connected to the testing apparatus for transmitting and receiving T(0,1) mode guided waves of FIG. 4. 4) The testing apparatus for transmitting and receiving T(0,1) mode guided waves of FIG. 4 were controlled so that guided waves that proceed to the right of the magnetostrictive transducer may be generated and a signal reflected from the right end of the pipe 80 might be detected. 5) The testing apparatus for transmitting and receiving T(0,1) mode guided waves of FIG. 4 was controlled so that driving signal amplitudes might be 3 V, 6 V, and 3V in a sequential order, and detected signal data was stored in the computer 70. 6) The transmission and received coil arrays (T-coils and R-coils) were removed, and residual magnetization was inducted using the permanent magnet and then the transmission and received coil arrays (T-coils and R-coils) were reinstalled. 7) The testing apparatus for transmitting and receiving T(0,1) mode guided waves of FIG. 4 was controlled so that driving signal amplitudes might be 3 V, 6 V, 11 V, 6 V and 3V in a sequential order, and the detected signal data was stored in the computer 70. 8) Stage 6) was repeatedly performed. 9) The testing apparatus for transmitting and receiving T(0,1) mode guided waves of FIG. 4 was controlled so that driving signal amplitudes might be 3 V, 6 V, 11 V, 27 V, 11 V, 6 V, and 3V in a sequential order, and the detected signal data was stored in the computer 70. 10) Stage 6) was repeatedly performed. 11) The testing apparatus for transmitting and receiving T(0,1) mode guided waves of FIG. 4 was controlled so that driving signal amplitudes might be 3 V, 6 V, 11V, 27 V, 52 V, 27 V, 11 V, 6 V, and 3V in a sequential order, and detected signal data was stored in the computer 70. 12) The transmission and received coil arrays (T-coils and R-coils) were removed and then, the transduction band was detached from pipe 80 so that experiments of the transduction band might be terminated. The permanent magnet used in the experiments was formed of a neodymium-iron-boron alloy, and a distance between centers of two poles, the length of each pole, and intensity of a magnetic field formed near each pole were 20 mm, 90 mm, and 0.6 T, respectively. The experimental procedures for the transduction band 300 of FIG. 1 were the same as those of other bands except that Stage 2) was replaced with connecting of two terminal of solenoid coil 312 to DC power supply (3 V, 6 V, 12 V, and 24 V) and Stages 6), 8), and 10) were not necessary.

FIG. 5 shows a typical example of the obtained signal data. The first echo is a main bang echo that is generated when a driving signal of T-coils is immediately detected by R-coils. The echoes that are generated in positions of 1 m, 2 m, and 3 m are echoes reflected from a right end and a left end of the pipe and the echo generated by the two guided waves that traveled the roundtrip distance of the pipe. The echo generated by direction-controlled guided waves, i.e., the echo reflected from the right end of the pipe, has the largest amplitude, and the other echoes have relative small amplitudes. The peak amplitude of the echo reflected from the right end of the pipe was measured from each signal data obtained by each magnetostrictive transducer so that reversibility of a response of the magnetostrictive transducer to the driving signal of the T-coils may be evaluated.

FIG. 6 shows results of evaluating reversibility of the magnetostrictive transducer using the conventional transduction band (not shown) that includes only a magnetostrictive strip. When the amplitude of the driving signal of the T-coils is less than or equal to 11 V, the conventional magnetostrictive transducer has comparatively good reversibility. However, as the amplitude of the driving signal of the T-coils is increased, the reversibility of the conventional magnetostrictive transducer is gradually lowered. A driving signal having an amplitude of 52 V causes a large change of residual magnetization in the magnetostrictive strip. As such, the reversibility of the conventional magnetostrictive transducer is greatly lowered. A driving signal having such as large amplitude may also be supplied to the T-coils while a user does not recognize the driving signal during operating of a testing system (in particular, while the testing system is turned on/off). Thus, considerable cautions are needed for correct operation of the magnetostrictive transducer using residual magnetization to form a bias magnetic field.

FIG. 7 shows results of the magnetostrictive transducer using the transduction band 300 of FIG. 1. A response of the magnetostrictive transducer to almost all of changes of a transmission coil driving signal and a bias voltage, i.e., a voltage at both ends of the solenoid coil 312, may be reversible. In case of the lowest bias voltage 3 V, a slightly irreversible response is measured. A received signal amplitude with respect to each driving signal voltage that is obtained when a driving signal voltage is increased is slightly smaller than a received signal amplitude with respect to each driving signal voltage that is obtained when the driving signal voltage is decreased. However, even in this case, a rapid decrease in the received signal amplitude at the large driving voltage that is measured when residual magnetization is used to form the bias magnetic field, does not occur. It is determined that minute irreversibility is caused by residual magnetization in the widthwise direction of a magnetostrictive strip due to large driving signals. In relatively large bias voltages, such minute irreversibility does not occur. This is because a large bias current is used to remove residual magnetization. The amplitude of the received signal is increased with the driving signal amplitude and the bias voltage. Nonlinear characteristic of an increase in the received signal amplitude with respect to the driving signal amplitude is increased with the bias voltage.

As described above, in a contact SH-guided-wave magnetostrictive transducer according to the present invention, a transduction band including a plate-shaped solenoid is used so that a uniform, robust and controllable bias magnetic field can be formed in a magnetostrictive strip without an additional unit and the contact SH-guided-wave magnetostrictive transducer having a reversible response to a change of a dynamic magnetic field can be constituted. An optimized contact SH-guided-wave magnetostrictive transducer that has a high reliability and gives a linear response to the change of the dynamic magnetic field can be used.

While this invention has been particularly shown and described with reference to exemplary embodiments thereof, it will be understood by those skilled in the art that various changes in form and details may be made therein without departing from the spirit and scope of the invention as defined by the appended claims.

The invention claimed is:

1. A contact shear horizontal (SH) mode guided-wave magnetostrictive transducer comprising:
   a transduction band which is disposed on a surface of an object to be tested and in which electromagnetic acoustic transduction occurs; and
   radio frequency (RF) coils disposed on the transduction band,
   wherein the transduction band comprises a plate-shaped solenoid comprising a magnetostrictive strip in which the electromagnetic acoustic transduction for transmitting or receiving SH mode guided waves occurs, and a solenoid coil wound in a spiral form along a circumference of the magnetostrictive strip so as to form a bias magnetic field in a lengthwise direction of the magnetostrictive strip, and
   the RF coils are used to form a dynamic magnetic field in a widthwise direction of the magnetostrictive strip or to detect a change of magnetic flux in the magnetostrictive strip.

2. The transducer of claim 1, wherein the transduction band is disposed to surround the object to be tested while being closely adhered to the surface of the object to be tested.

3. The transducer of claim 1, wherein the solenoid coil surrounds the circumference of the magnetostrictive strip uniformly and form a uniform and controllable bias magnetic field with respect to the lengthwise direction of the magnetostrictive strip.

4. The transducer of claim 1, wherein the transduction band further comprises a non-ferromagnetic metal strip disposed to be acoustically coupled to a lower surface of the plate-shaped solenoid so that a shape of the transduction band is maintained and the magnetostrictive strip and the solenoids are prevented from being damaged.

5. The transducer of claim 4, wherein the transduction band further comprises a contact layer coated on a lower surface of the non-ferromagnetic metal strip and comprising a non-stickiness material that allows the transduction band to be repeatedly attached and detached to and from the surface of the object to be tested and the transduction band to be reused, and the contact layer comprises material having an excellent transverse wave propagation characteristic and an electrical insulation property.

6. The transducer of claim 1, wherein the transduction band further comprises a contact layer coated on a lower surface of the plate-shaped solenoid and comprising a non-stickiness material that allows the transduction band to be repeatedly attached and detached to and from the surface of the object to be tested and the transduction band to be reused, and the contact layer comprises material having a excellent transverse wave propagation characteristic and an electrical insulation property.

7. The transducer of claim 4, wherein the object to be tested comprises a cylindrical structure having a circular cross-section, and the transduction band contacts the surface of the object to be tested and has a ring-shaped cross-section in which both ends of the transduction band face each other, and
   as the non-ferromagnetic metal strip has a larger length than that of the magnetostrictive strip, when the non-ferromagnetic metal strip is adhered to the lower surface of the plate-shaped solenoid and is coupled to the lower surface of the plate-shaped solenoid, both ends of the non-ferromagnetic metal strip are exposed to the outside, and
   the transduction band comprises:
   a contact layer disposed between the surface of the object to be tested and the lower surface of the non-ferromagnetic metal strip; and
   a clamping unit for coupling the both ends of the non-ferromagnetic metal strip.

8. The transducer of claim 7, wherein the both ends of the non-ferromagnetic metal strip are respectively bent and form a pair of ring portions for facing each other, and
   the clamping unit comprises:
   a pair of cylinders in which through holes through which bolts are tightened are formed and which are inserted in the pair of ring portions; and
   a bolting unit for tightly coupling the pair of metal cylinders through the through holes.

9. The transducer of claim 7, wherein the contact layer comprises metal or plastic that is easily deformable and flexible so that acoustic coupling between the object to be tested and the non-ferromagnetic metal strip is easily performed.

10. The transducer of claim 2, wherein the transduction band further comprises a non-ferromagnetic metal strip disposed to be acoustically coupled to a lower surface of the plate-shaped solenoid so that a shape of the transduction band is maintained and the magnetostrictive strip and the solenoids are prevented from being damaged.

11. The transducer of claim 3, wherein the transduction band further comprises a non-ferromagnetic metal strip disposed to be acoustically coupled to a lower surface of the plate-shaped solenoid so that a shape of the transduction band is maintained and the magnetostrictive strip and the solenoids are prevented from being damaged.

* * * * *